(12) United States Patent
Warmath et al.

(10) Patent No.: US 8,116,549 B2
(45) Date of Patent: Feb. 14, 2012

(54) METHOD AND APPARATUS FOR STANDARDIZING ULTRASONOGRAPHY TRAINING USING IMAGE TO PHYSICAL SPACE REGISTRATION OF TOMOGRAPHIC VOLUMES FROM TRACKED ULTRASOUND

(75) Inventors: John Warmath, Nashville, TN (US); Alan Herline, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/982,510

(22) Filed: Dec. 30, 2010

(65) Prior Publication Data
US 2011/0098569 A1    Apr. 28, 2011

Related U.S. Application Data

(62) Division of application No. 11/535,648, filed on Sep. 27, 2006, now Pat. No. 7,912,258.

(60) Provisional application No. 60/720,813, filed on Sep. 27, 2005.

(51) Int. Cl.
*G06K 9/00* (2006.01)
(52) U.S. Cl. .......................... 382/131; 382/128; 382/154
(58) Field of Classification Search .............. 382/128, 382/130, 131, 154; 600/10, 407, 433, 426, 600/425, 437; 324/309; 128/922; 250/455
See application file for complete search history.

(56) References Cited

U.S. PATENT DOCUMENTS

| | | | |
|---|---|---|---|
| 5,609,485 A * | 3/1997 | Bergman et al. | 434/262 |
| 5,956,418 A | 9/1999 | Aiger et al. | |
| 6,006,126 A | 12/1999 | Cosman | |
| 6,159,152 A | 12/2000 | Sumanaweera et al. | |
| 6,210,168 B1 | 4/2001 | Aiger et al. | |
| 6,390,982 B1 | 5/2002 | Bova et al. | |
| 6,546,279 B1 | 4/2003 | Bova et al. | |

(Continued)

FOREIGN PATENT DOCUMENTS
WO    03039370 A1    5/2003

OTHER PUBLICATIONS

Medsim Advanced Simulation, http://www.medsim.com/profile/company.html, publication date—unknown, found Jun. 22, 2005 (pp. 1-4).

(Continued)

*Primary Examiner* — Samir Ahmed
*Assistant Examiner* — Ali Bayat
(74) *Attorney, Agent, or Firm* — Panitch Schwarze Belisario & Nadel LLP

(57) ABSTRACT

A clinical and training apparatus that collects and processes physical space data while performing an image-guided procedure on an anatomical area of interest includes a calibration probe, a tracked ultrasonic probe, a wireless tracking device that tracks the ultrasonic probe in space and an image data processor. The physical space data provides three-dimensional coordinates for each of the physical points. The image data processor includes a memory holding instructions. The instructions include determining registrations used to indicate position in image space and physical space; using the registrations to map into image space, image data describing the physical space of the tracked ultrasonic probe and the anatomical area of interest; and constructing a three-dimensional (3D) volume based on ultrasonic image data. The apparatus includes a storage medium that stores a plurality of 3D volumes acquired by the image data processor for later retrieval.

3 Claims, 12 Drawing Sheets

U.S. PATENT DOCUMENTS

| | | | |
|---|---|---|---|
| 6,584,339 | B2 * | 6/2003 | Galloway et al. ............. 600/426 |
| 6,591,130 | B2 | 7/2003 | Shahidi |
| 2002/0062077 | A1 | 5/2002 | Emmenegger et al. |
| 2002/0193687 | A1 | 12/2002 | Vining et al. |
| 2004/0019274 | A1 | 1/2004 | Galloway et al. |
| 2004/0059217 | A1 | 3/2004 | Kessman et al. |
| 2005/0010098 | A1 | 1/2005 | Frigstad et al. |
| 2005/0063575 | A1 | 3/2005 | Ma et al. |
| 2005/0111761 | A1 | 5/2005 | Mathew et al. |
| 2006/0241432 | A1 | 10/2006 | Herline et al. |
| 2008/0132785 | A1 | 6/2008 | Piron et al. |

OTHER PUBLICATIONS

Bao, P., et al., "Ultrasound to computed tomography registration for image-guided laparoscopic liver surgery," Endoscopy, Springer-Verlag 2005 (Jan. 2005).

Warmath, J.R., et al., "Use of 3-D Freehand Endorectal Ultrasound System With Appropriate Rectal Phantom," Int'l Conf., IEEE EMBS (Sep. 17-21, 2003).

Warmath, J.R. et al., "Development of a 3-D freehand endorectal ultrasound system for use in rectal cancer imaging," Medical Physics, vol. 32, pp. 1757-1766 (May 25, 2005).

Warmath, J.R., "Ultrasound 3-D Volume Reconstruction from an Optically Tracked Endorectal Ultrasound (TEREUS) Probe," Light-Emitting Diodes: Research, Manufacturing and Applications, VIII Edition, SPIE vol. 5367, pp. 228-236 (May 2004).

Boa, P., et al., "Tracked Ultrasound for Laparoscopic Surgery," Medical Imaging 2004: Visualization, Image-Guided Procedures and Display, SPIE vol. 5367, pp. 237-246 (May 2004).

Office Action dated Apr. 6, 2010 in prior U.S. Appl. No. 11/535,648.
Office Action dated Jul. 8, 2010 in prior U.S. Appl. No. 11/535,648.
Office Action dated Nov. 12, 2010 in prior U.S. Appl. No. 11/535,648.

* cited by examiner

METHOD AND APPARATUS FOR STANDARDIZING ULTRASONOGRAPHY TRAINING USING IMAGE TO PHYSICAL SPACE REGISTRATION OF TOMOGRAPHIC VOLUMES FROM TRACKED ULTRASOUND

CROSS REFERENCE TO RELATED APPLICATIONS

This application is a divisional application of U.S. patent application Ser. No. 11/535,648, filed on Sep. 27, 2006, entitled "Method and Apparatus for Standardizing Ultrasonography Training Using Image to Physical Space Registration of Tomographic Volumes from Tracked Ultrasound," currently pending, which claims priority to U.S. Provisional Patent Application No. 60/720,813 filed on Sep. 27, 2005 entitled "Method and Apparatus for Standardizing Ultrasonography Training Using Image to Physical Space Registration of Tomographic Volumes from Tracked Ultrasound," the entire contents of all of which are incorporated by reference herein.

BACKGROUND OF THE INVENTION

The present invention relates to a method and apparatus for standardizing ultrasonography training, and more particularly, a method and apparatus for standardizing ultrasonography training using image to physical space registration of tomographic volumes from tracked ultrasound.

There are a number of medical imaging and instrumentation systems presently available including Positron Emission Tomography (PET), Magnetic Resonance Imaging (MRI), computed tomography (CT) and ultrasound. CT and MRI are imaging modalities that provide tomographic slices of the imaged volume.

CT and/or MRI used in combination with other imaging modalities, provide more useful information for the staging and treatment of cancer. For example, using CT and ultrasound can provide better diagnostics as well as the potential for spatial orientation of the patient and/or the area of interest.

A fundamental force in the development of surgery and other forms of directed therapy is the need to increase the information available to physicians and to place that information in both spatial and temporal contexts. The field of interactive image guided procedures (IGP), as it is known today, began in the 1980's and focused on tracking the surgical position in the physical space and display position in image space. This technique was first used in the field of neurosurgery and eventually crossed over into many other medical fields. IGPs have four basic components including image acquisition, image-to-physical-space registration, three-dimensional tracking, and display of imaging data and location. There has been much concurrent advancement in these four areas, which is a necessity for the timely incorporation of IGP into common medical practice.

A system of interest utilizes a scan technology such as CT in combination with an ultrasound instrument, such as an endorectal ultrasound (ERUS) probe, that is tracked for position in physical space in order to display position in image space. Such a system provides much more diagnostic information, but training students and technicians on even general ultrasonography is a somewhat complicated undertaking. Ultrasound image interpretation is associated with a significant learning curve.

Currently practical, as opposed to didactic, ultrasonography training is performed by trainees practicing on live patients and then learning disease processes from mentors. The training is serendipitous at best since a trainee practices only on the available test patients and not a wide variety of test patients suffering from a wide variety of diseases or disorders. The current approach to training in ultrasonography generally utilizes classroom training and education in the theory and physics of ultrasound measurements. Once this is completed the trainee goes through extended on the job training by practicing and learning on real patients under the guidance of an experienced radiologist. In some specialties this may require working with 50 to 100 patients. In a clinical setting, the flow of patients is irregular and unpredictable. Therefore, the duration of training is unpredictable. By using the time of a radiologist or other skilled imaging specialist along with the trainee, the time and cost expended is significant by the time the trainee is sufficiently "certified" to independently acquire and/or interpret images.

Thus, presently available ultrasonography training is provided with models that may not be realistic and certainly are limited by the number and expense of multiple models with which to train. There are more than 25,000 registered ultrasound technicians. There are different specialties within ultrasonography. The testing is standardized and involves static exams after a training and schooling period. Thus, it is desirable to provide an ultrasonography training system that permits the trainee to view more images of particular areas of interest for specialization and for improving training.

One ultrasound training system is disclosed in U.S. Pat. No. 5,609,485 (Bergman et al.). Bergman et al. disclose a medical "reproduction system" for use in training. The medical reproduction system is a computer-based, interactive system for use by physicians and technicians in medical training and diagnosis by means of medical instrumentation such as ultrasound machines. The system of Bergman et al. collects ultrasound data and creates a training system using simulated tools (e.g., ultrasound machine, transducer and mannequin). Bergman et al. suggest that the system can be used for offline diagnosis by a technician or physician at some time after an actual patient scan or ultrasound. However, Bergman et al. does not provide an assessment of the accuracy of the acquired ultrasound volumes, and therefore, there is no detail as to how the system would be useful as a clinical diagnostic tool.

It is desirable to provide a method and apparatus for standardizing ultrasonography training using image to physical space registration of tomographic volumes from tracked ultrasound. It is desirable to provide a technology that would shorten, standardize, and broaden the training for technicians as well as radiologists and surgeons. It is desirable to use "spatially-oriented" ultrasound images for training of physicians, technicians and nurses in the use and interpretation of ultrasound images for various portions of the anatomy.

BRIEF SUMMARY OF THE INVENTION

Briefly stated, the present invention comprises an apparatus and method for calibration, tracking and volume construction data for use in image-guided procedures. In one embodiment, the present invention comprises an apparatus that collects and processes physical space data while performing an image-guided procedure on an anatomical area of interest. The apparatus includes a calibration probe that collects physical space data by probing a plurality of physical points, a tracked ultrasonic probe that outputs two-dimensional ultrasonic image data, a tracking device that tracks the ultrasonic probe in space and an image data processor comprising a computer-readable medium. The physical space data provides three-dimensional (3D) coordinates for each of the physical points. The computer-readable medium holds computer-executable instructions that includes determining registrations used to indicate position in both image space and physical space based on the physical space data collected by the calibration probe; using the registrations to map into image space, image data describing the physical space of the tracked ultrasonic probe used to perform the image-guided procedure and the anatomical area of interest; and constructing a three-dimensional volume based on the two-dimensional ultrasonic image data on a periodic basis.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
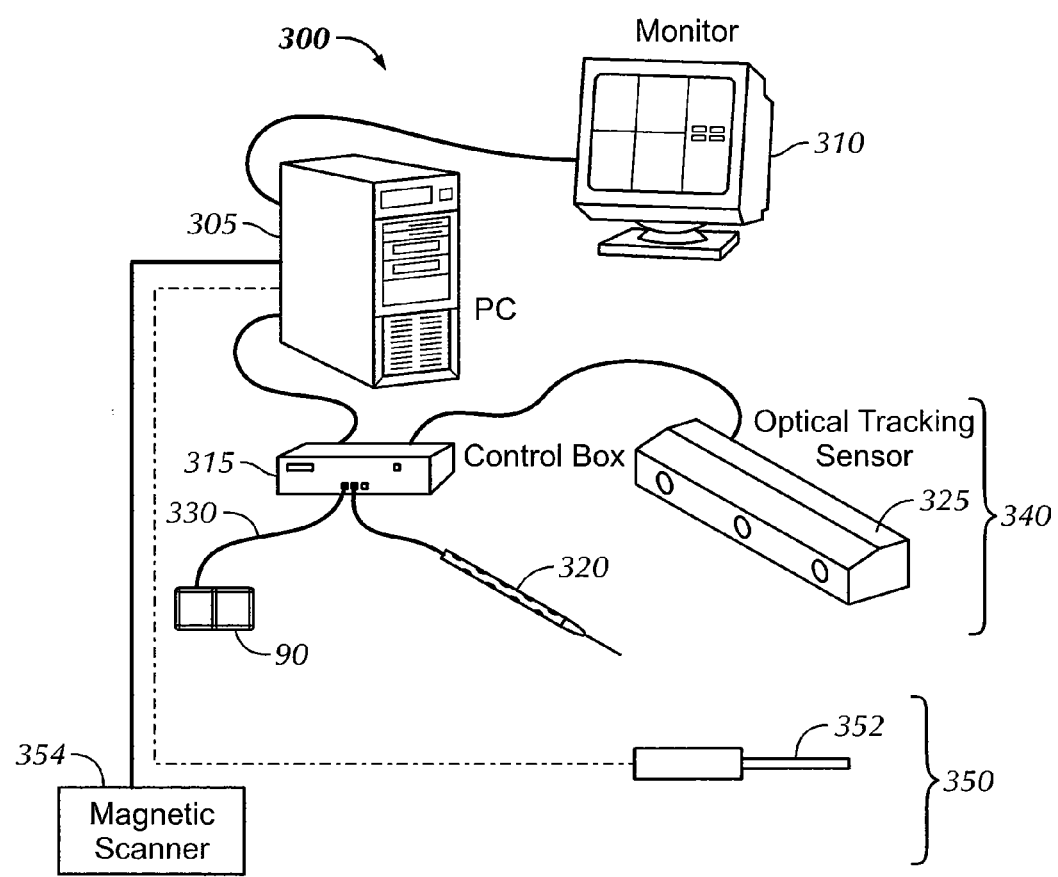
FIG. 1 shows a schematic block diagram of a hardware system for one possible configuration of an image-guided procedure tracking system in accordance with preferred embodiments of the present invention.

Certain terminology is used in the following description for convenience only and is not limiting. The words "right", "left", "lower", and "upper" designate directions in the drawings to which reference is made. The words "inwardly" and "outwardly" refer direction toward and away from, respectively, the geometric center of the object discussed and designated parts thereof. The terminology includes the words above specifically mentioned, derivatives thereof and words of similar import. Additionally, the word "a", as used in the claims and in the corresponding portions of the specification, means "one" or "at least one."

Preferred embodiments of the present invention include Image Guided Procedures (IGP). IGP have four basic components: image acquisition, image-to-physical-space registration, three-dimensional tracking, and display of imaging data and location. A relevant IGP system is disclosed in U.S. Pat. No. 6,584,339 B2 (Galloway, Jr. et al.), the contents of which is incorporated by reference herein. In IGP, physical space data provides three-dimensional (3D) coordinates for each of the physical surface points. Based on the physical space data collected, point-based registrations used to indicate position in both image space and physical space are determined. The registrations are used to map into image space, image data describing the physical space of an instrument used to perform the IGP, an anatomical region of interest and a particular portion to be studied (e.g., a tumor or growth). The image data is updated on a periodic basis.

Further, preferred embodiments of the present invention utilize an optically tracked two dimensional (2D) ultrasound probe to acquire a 2D image(s). Additionally, preferred embodiments of the present invention may also utilize an optically tracked 3D ultrasound to acquire 2D or 3D image(s). Embodiments of the present invention therefore permit the creation of a 3D ultrasound volume from 2D tracked ultrasound data and creation of a 3D ultrasound volume from 3D tracked ultrasound data. Acquired imaging scans (e.g., Computed Tomography (CT) scans) can be used as a comparison and/or in conjunction with pre-operative and inter-operative 3D ultrasound volume sets. The 3D ultrasound volume sets provide the ability to be tracked over time.

Embodiments of the present invention include the creation of a 3-D ultrasound image volume set from tracked ultrasound data and allow for physical space registration to patients. While described herein as use with an endorectal ultrasound (ERUS) or tracked endorectal ultrasound (TERUS) probe 352 (FIG. 1), embodiments of the present invention are not limited thereto. The concepts embraced by the embodiments of the present invention can be utilized with other ultrasound technologies and/or in other systems that provide "spatially-oriented" ultrasound images. Embodiments of the present invention may work in a range of ultrasound applications including echocardiography, cardiovascular ultrasounds, renal ultrasounds, obstetric ultrasounds, abdominal ultrasounds, breast ultrasounds, gallbladder ultrasounds, transrectal ultrasounds, transvaginal ultrasounds or the like.

Various embodiments of the present invention include (i) a training simulation tool using detailed spatially oriented images, (ii) a clinical tool using real time spatially oriented images with IGS; and (iii) methods of developing a spatially oriented image library(ies).

By creating an ultrasound volume set and accomplishing a registration to the physical space of the patient, more diverse ultrasonography training can be provided by using the same patient and changing image sets thereby creating a "virtual trainer" for ultrasound. The motion of the ultrasound probe 352 is not generally as important to the training process, unlike virtual surgical training, as much as the image information analysis and interpretation. Preferably, libraries of ultrasound images are created so that a student, such as an ultrasound technician, radiology resident or a surgeon, can choose multiple sets of data to focus in certain areas. For example, libraries of data may include pluralities of breast ultrasounds, gallbladder ultrasounds, transrectal ultrasounds, transvaginal ultrasounds, disease or trauma ultrasounds or tumor ultrasounds in certain areas. The technology has the ability to lessen the cost of training, improve the accreditation process and remain applicable in all fields of ultrasonography.

Figure 13:
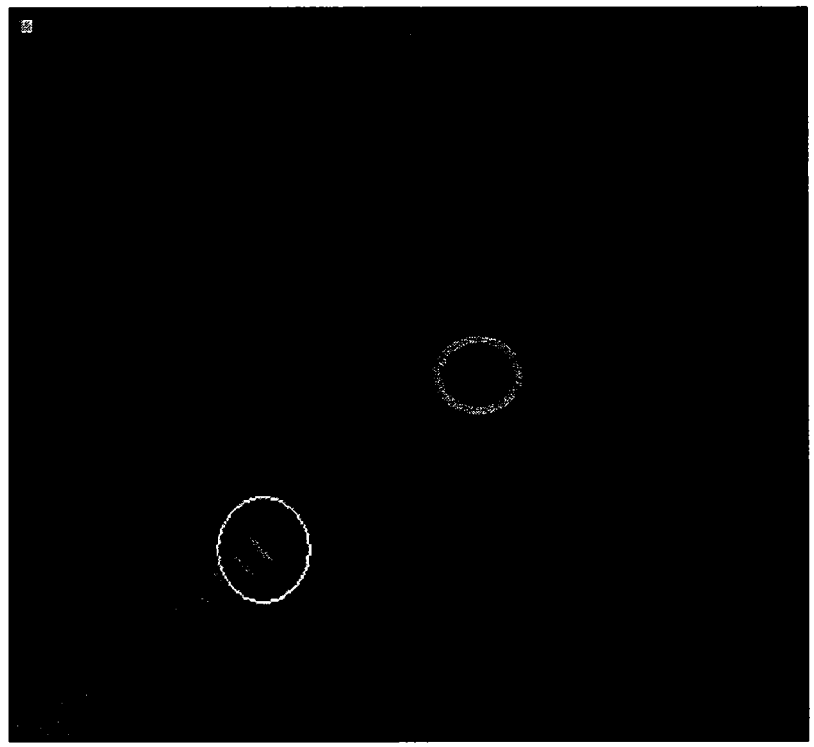
FIG. 13 is an ultrasonic image showing a tip of a calibration probe acquired by a tracked endorectal ultrasonic (TERUS) probe during a calibration procedure in accordance with the preferred embodiments of the present invention.

Currently, various modules exist to acquire data and produce spatially oriented 3D images and volumes from a multitude tracked ultrasonic probes 352. Volumes collected across a patient population can be used to train ultrasound users who would otherwise not have access to such a large set of images. For example, students could train using a kidney cancer volume set without having to scan a patient with kidney cancer. This allows for increased experience before a student actually performs an ultrasound exam clinically. A technician can learn the proper techniques to acquire valid images (see FIG. 13) that can be readily interpreted by a physician. Residents learn both the proper acquisition and interpretation of ultrasound images. In some cases, particularly obstetrics/gynecology (OB/GYN), nurses will acquire and assist in interpretation of the images.

Besides ease of use, optical tracking has an advantage over the other 3D acquisition methods which is a result of coordinate integrated imaging. When using a tracked ultrasonic device, such as a TERUS probe 352 (FIG. 1), the exact location and orientation of the probe 352 are known. Through the process of calibration, the location and orientation of the ultrasound beam are also known in an external coordinate space. This allows each pixel in the ultrasound data set to be assigned a 3D coordinate value in a physical space that is related to the ultrasound space through a specific transformation matrix. This method of assigning coordinate values to the ultrasound data in physical space has two advantages. First, it allows the direct comparison of two imaging modalities. This is achieved by transforming a data set, such as CT, into the same physical space as the ultrasound, making an accurate comparison possible. Second this method allows localization of multiple tools and image sets into the same physical space. The user then has the ability to guide a tracked instrument, such as a biopsy needle or surgical instrument, to a specific location in physical space while at the same time viewing the progress in all imaging modalities (i.e., ultrasound and CT). These co-registration and guidance techniques are not possible using the mechanical 3D volume reconstruction methods because multiple image sets and surgical tools cannot be localized in the same physical space. The mechanical based methods are appropriate for 3D volume reconstruction of ultrasound data, but are not valid for anything beyond visual enhancement of the rectum.

Referring to FIG. 1, an apparatus 300 that collects and processes physical space data while performing an image-guided procedure on an anatomical area of interest includes a calibration probe 320 that collects physical space data by probing a plurality of physical points, a tracked ultrasonic probe 352 that outputs ultrasonic image data (2D or 3D), a tracking device 325 that tracks the ultrasonic probe 352 in space and an image data processor 305 comprising a computer-readable medium (e.g., memory, FlashRAM, hard disk, etc.). The physical space data provides 3D coordinates for each of the physical points. The computer-readable medium 305 holds computer-executable instructions that include determining registrations used to indicate position in both image space and physical space based on the physical space data collected by the calibration probe 320. The instructions further include using the registrations to map into image space image data describing the physical space of the tracked ultrasonic probe 352 used to perform the image-guided procedure and the anatomical area of interest. The instructions also include constructing a 3D volume based on the 2D or 3D ultrasonic image data on a periodic basis.

Figure 2:
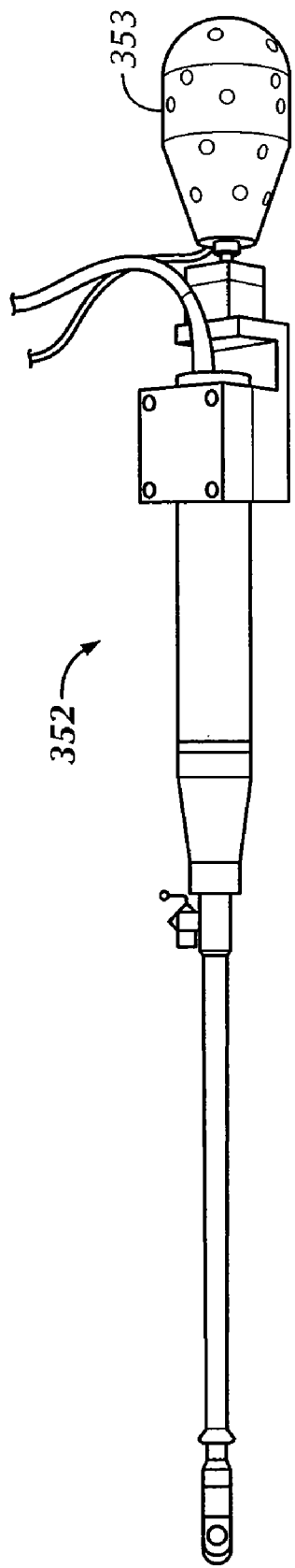
FIG. 2 is a perspective photographic view of a tracked endorectal ultrasonic (TERUS) probe for use with preferred embodiments of the present invention.

In one preferred embodiment of the present invention described using FIG. 1, an optically tracked endorectal ultrasound (TERUS) probe 352 is utilized for improving the care of rectal cancer. While described herein as used with a TERUS probe 352, embodiments of the present invention are not limited thereto. ERUS images are intrinsically different from images taken by CT or MRI in that ultrasound provides 2D images while CT and MRI provide 3D data sets that can be viewed as 2D images. By optically tracking the TERUS probe 352, one may overcome the limitations of 2D ultrasound and improve the diagnosis and care of patients with rectal cancer. The TERUS probe 352 may be a 360-degree rotating BK 1850 TERUS probe 352 (FIG. 2) commercially available from B-K Medical, Herlev, Denmark.

Figure 4:
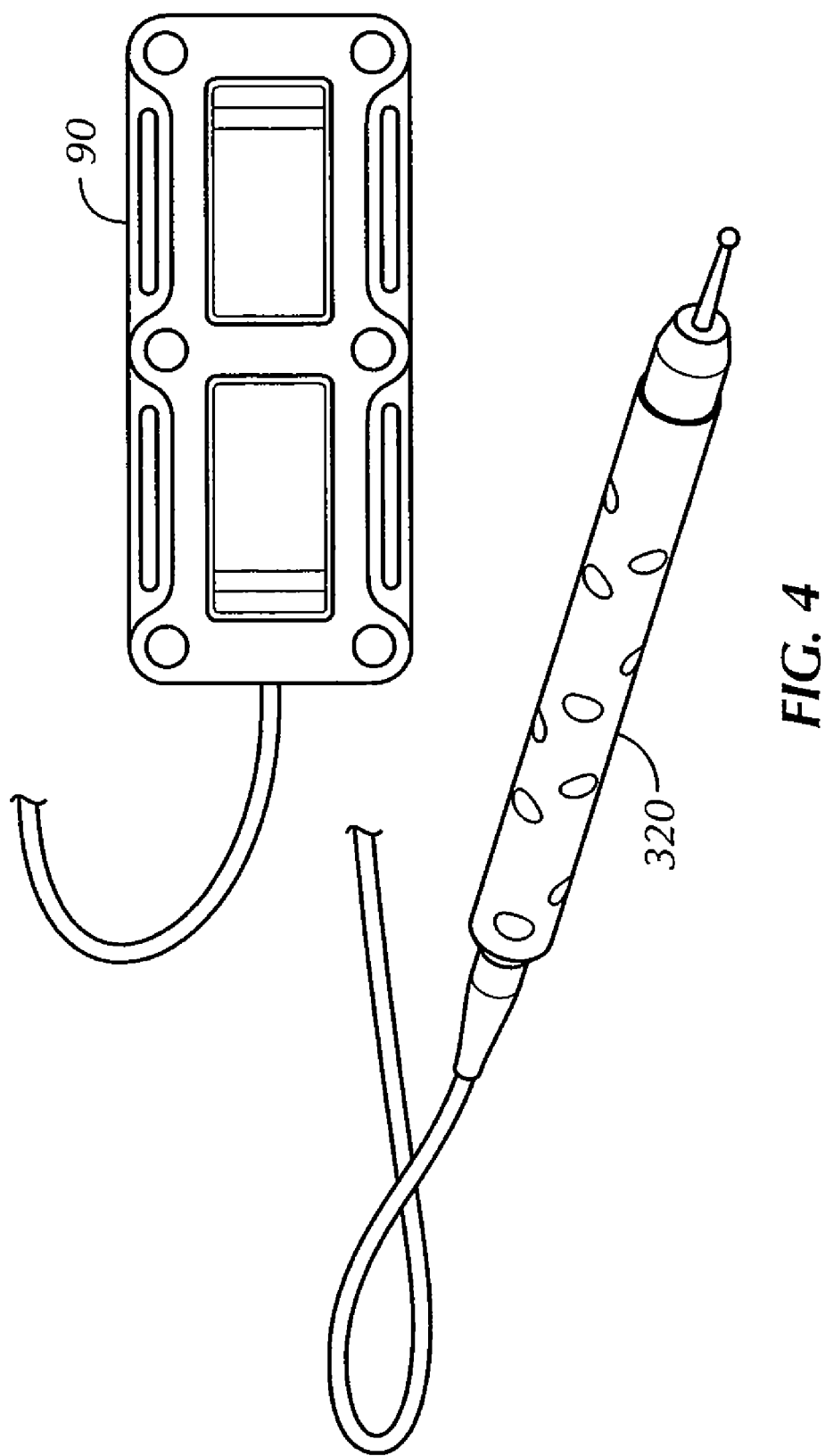
FIG. 4 is a perspective photographic view of a calibration probe and a reference emitter for an optically tracked system, each having a plurality of infrared emitting diodes (IREDs) disposed thereon for use with the image-guided procedure tracking system of FIG. 1.
Figure 5:
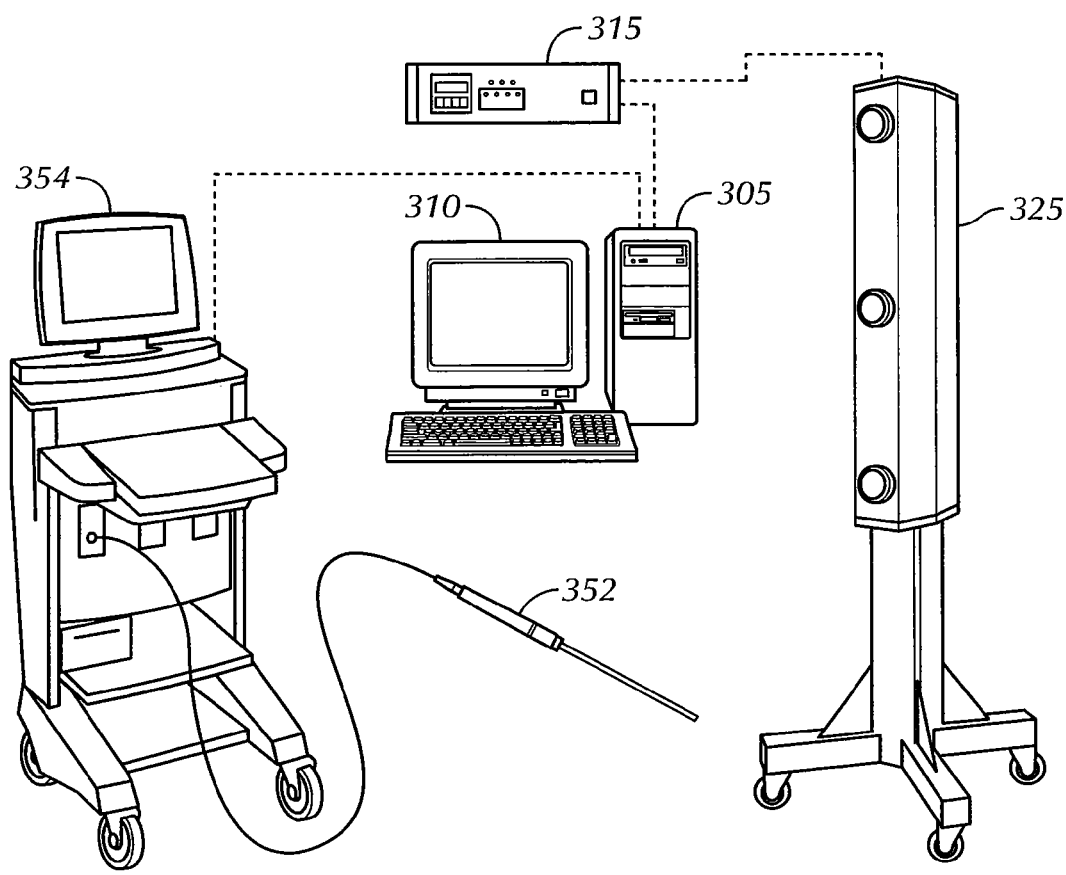
FIG. 5 is a perspective photographic view of an image-guided procedure tracking system in accordance with preferred embodiments of the present invention.

FIG. 1 shows that the ultrasound-based IGP system 300 includes an endorectal ultrasound probe 352 with an attached "gear shift knob" rigid body 353 (shown in FIG. 2), an ultrasound machine 354, a reference emitter 90, a calibration probe 320 and an optical tracking localization system 340. The reference emitter 90 establishes an overall 3D coordinate system. The ultrasound machine 354 may be a BK Falcon 2101 commercially available from B-K Medical (FIG. 5). The calibration probe 320 (FIG. 4) may be a pen probe commercially available from Northern Digital, Waterloo, Ontario, Canada. The optical tracking localization system 340 may be an Optotrak 3020 commercially available from Northern Digital.

The optical tracking system 340 determines triangulated position data based on emissions from a plurality of infrared emitting diodes (IREDs) distributed over the surface of a handle of the calibration probe 320, the TERUS probe 352 and/or another instrument. The optical tracking system 340 includes the optical tracking sensor 325 and optionally an optical reference emitter 90. The optical tracking sensor tracks the IREDS that are disposed on the handle of the calibration probe 320 and IREDS disposed on the reference emitter 90. The reference emitter 90 is rigidly or semi-rigidly attached to the patient. FIGS. 1 and 4 show a rectangularly shaped reference emitter 90, but other shaped reference emitters 90 may be utilized such as a cross-shape reference emitter 90' (FIG. 7) and the like. The plurality of IREDs emit a plurality of intermittent infrared signals used to triangulate the position of the calibration probe 320 in 3-D image space. By using the point-based registrations and the triangulated position data to map into image space, image data describing the physical space of the distal end of the TERUS probe 352 can also be used to perform the IGP and to update the image data on a periodic basis. Other image-tracking systems such as binocular-camera systems may be utilized without departing from the present invention.

Figure 7:
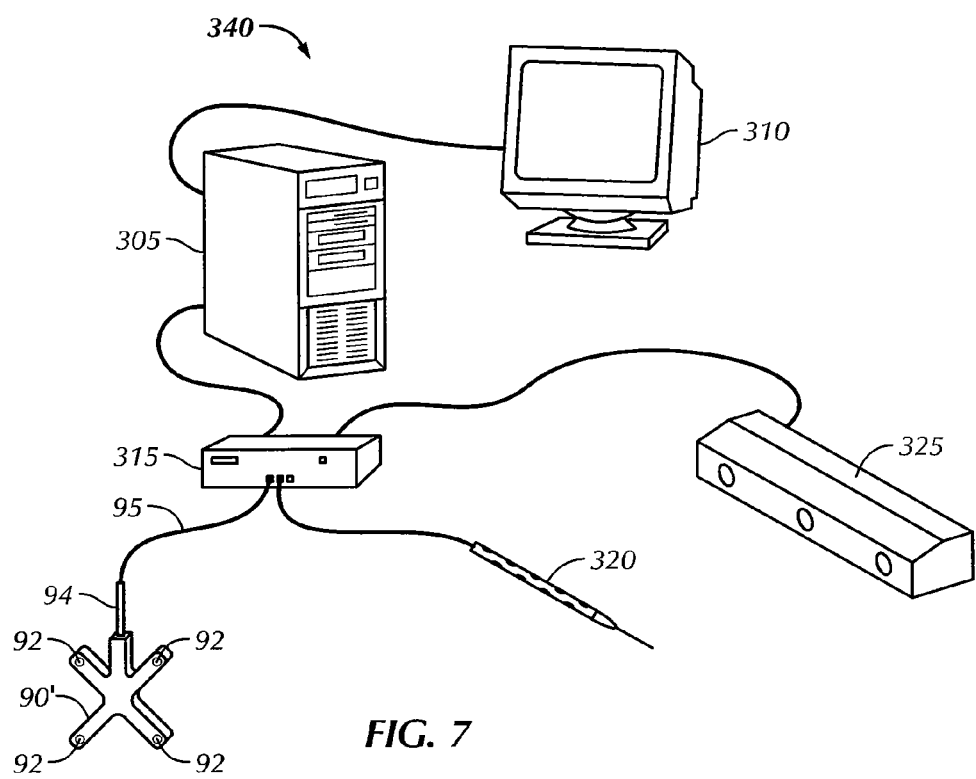
FIG. 7 shows a schematic block diagram of a hardware system for one possible configuration of an optical tracking system in accordance with preferred embodiments of the present invention.
Figure 8:
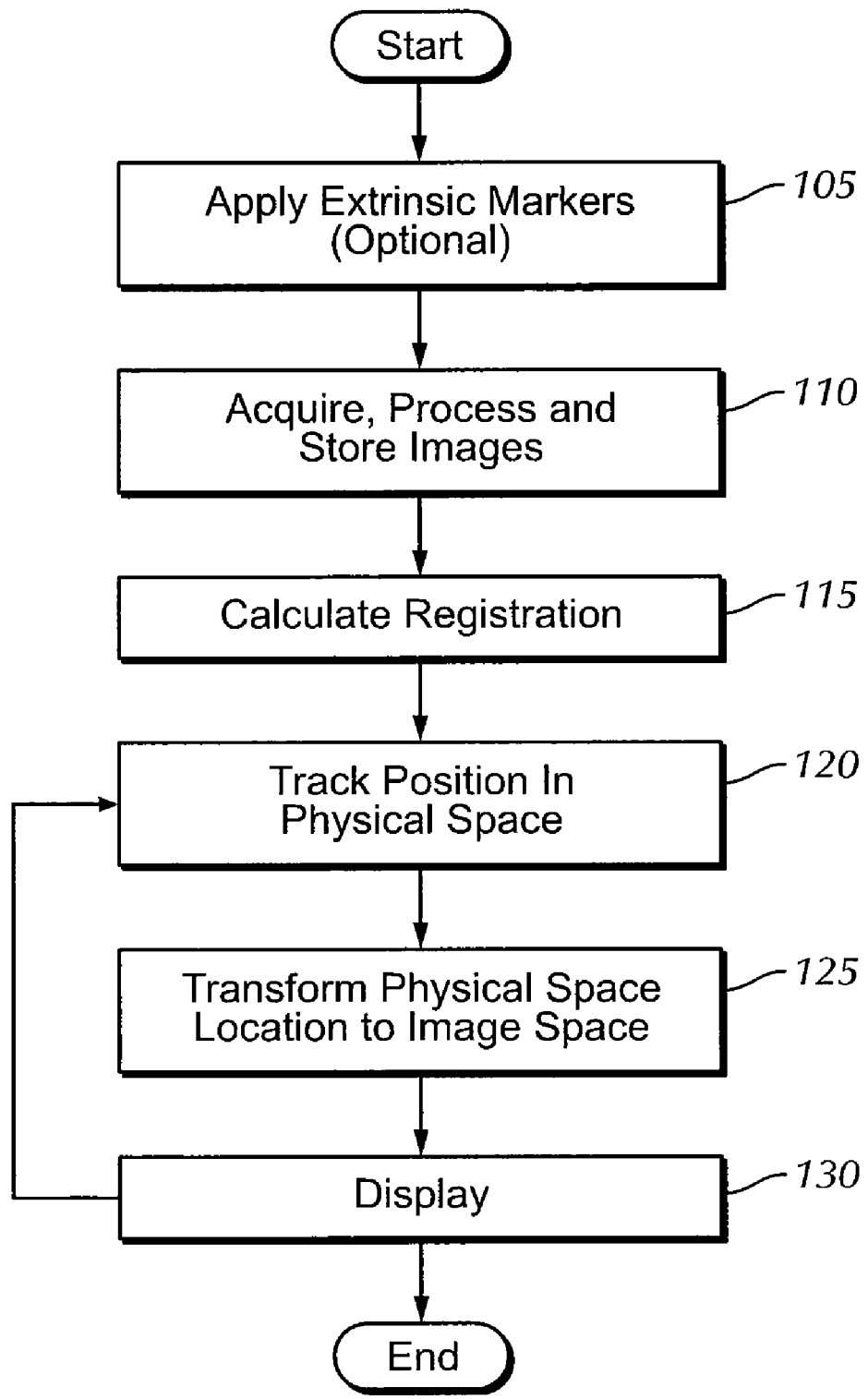
FIG. 8 shows a general flow chart for an image-guided tracking system in accordance with preferred embodiments of the present invention.

FIGS. 1 and 7 show that the optical tracking localization system 340 includes a control box 315 to interface with a computer 305. The software program that allows the integration of the components may be an operating room image-oriented navigation system (ORION), which was developed in the Surgical Navigation and Research Laboratory (SNARL) lab at Vanderbilt University, Nashville, Tenn. ORION may be implemented in Windows NT using MS Visual C++6.0 with the Win32 API. ORION was originally developed in Windows NT and is running on a 400 MHz processor personal computer (i.e., an image data processor) 305 with 256 MB of memory and a display monitor 310. However, other operating systems and processors may be utilized. The computer 305 may also include two specialized cards such as a VigraVision-PCI card (commercially available from VisiCom Inc., Burlington, Vt.) which is a combination color frame grabber and accelerated SVGA display controller which is capable of displaying NTSC video images in real time, and an ISA high-speed serial port card communicates with the calibration probe 320 via the control box 315. Of course, the computer 305 may include the necessary interfaces and graphics drivers without the need from specialized cards. For example, optical tracking system 340 may include network connections such as Ethernet, infrared (IR), wireless (Wi-Fi), or may include bus adapters such as parallel, serial, universal serial bus (USB) and the like.

Figure 9:
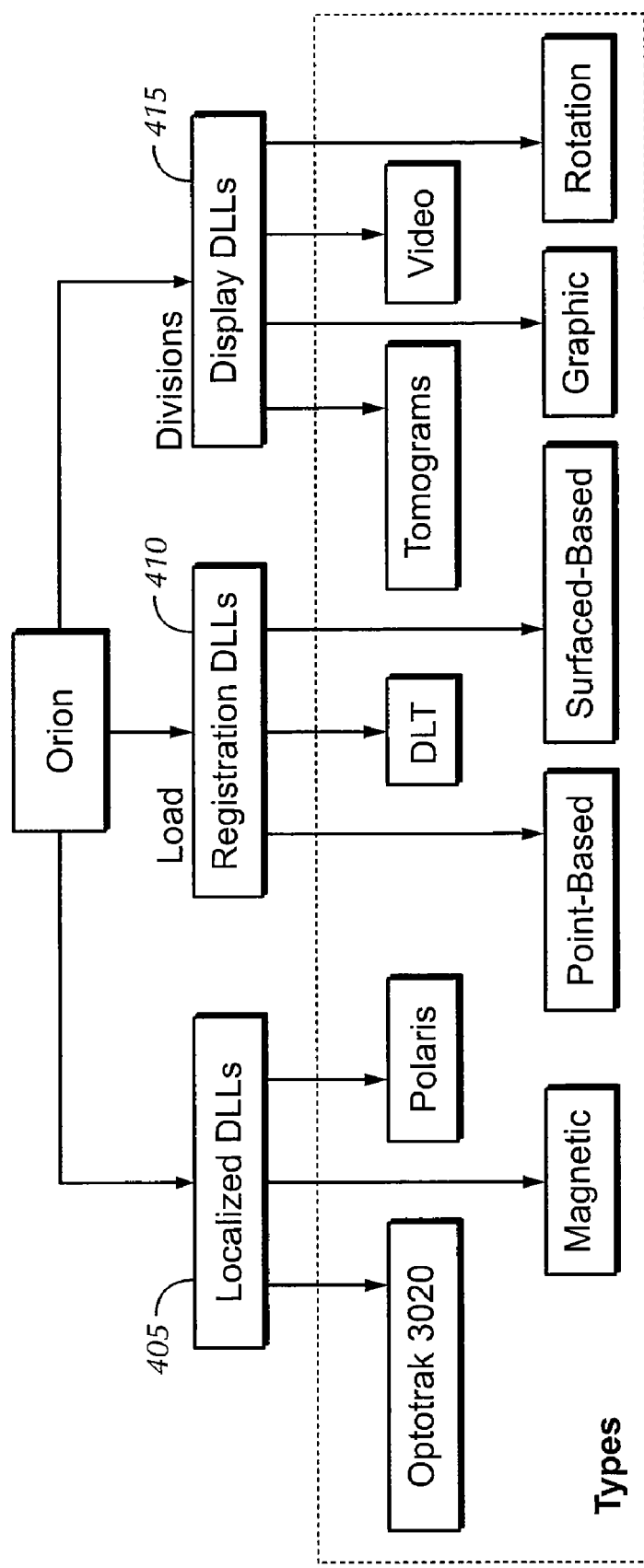
FIG. 9 shows a basic software architecture for one possible configuration of an image-guided tracking system in accordance with preferred embodiments of the present invention.
Figure 10:
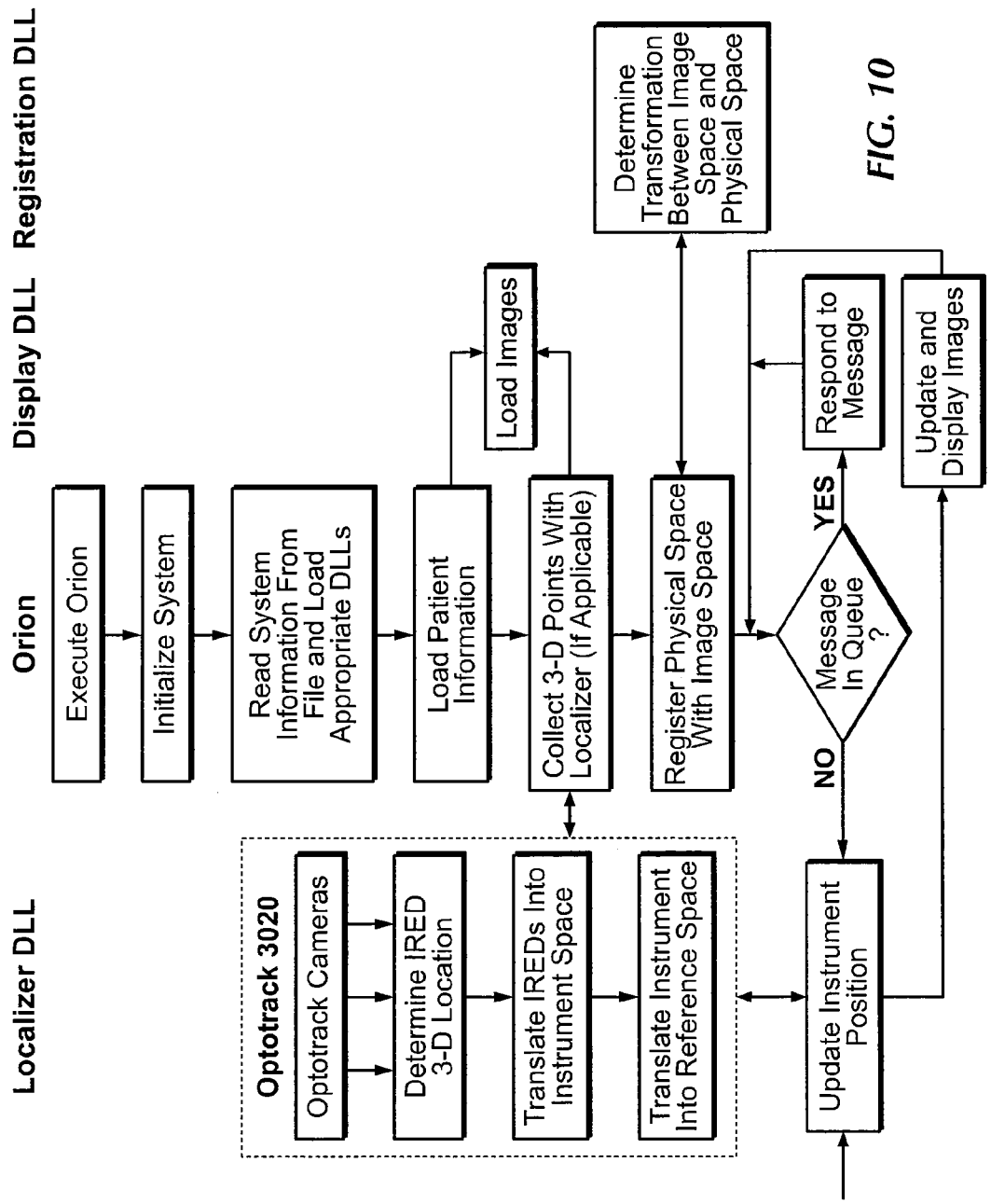
FIG. 10 shows a general flow chart for an image-guided tracking system for one possible configuration of an image-guided tracking system in accordance with preferred embodiments of the present invention.

FIG. 9 shows a basic software architecture for one possible configuration of an image-guided tracking system 340 in accordance with preferred embodiments of the present invention. The software may include dynamic link libraries (DLLs) such as localizer DLLs 405, registration DLLs 410 and display DLLs 415. FIG. 10 shows a general flow chart for an image-guided tracking system for one possible configuration of an image-guided tracking system in accordance with preferred embodiments of the present invention.

Other hardware, operating systems, software packages, and image tracking systems may utilized without departing from the present invention.

Figure 6:
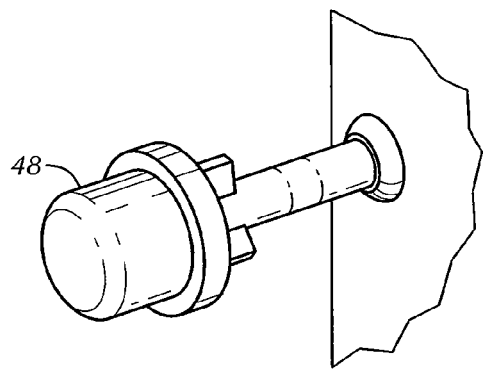
FIG. 6 a perspective view of a fiducial marker for use with the image-guided procedure tracking system of FIG. 1.

Locations of targets are found using two different imaging modalities, CT and ultrasound, and the target registration error (TRE) between these two image sets are calculated. Fiducial markers 48 (FIG. 6) are used for image registration. The fiducial markers 48 may either be skin markers such as those commercially available from Medtronics, Inc., Minneapolis, Minn., or bone implant markers such as those commercially available from ZKAT, Hollywood, Fla. The fiducial markers 48 are utilized to localize in the images using image processing routines and then touch using an optical tracker in the operating room. The positions of the fiducial markers 48 are recorded and then a point registration is performed using either a quaternion based or singular-value-decomposition-based algorithm. Fiducial divot caps are used for finding the location of the fiducial markers 48 in physical space and fiducial CT caps are used for finding the location of the fiducial markers 48 in CT space. These fiducial caps are interchangeable and an appropriate type is chosen depending on the desired imaging modality. Preferably, non-planar fiducial markers 48 are used to align the CT and Ultrasound images in a rigid registration process.

Figure 3:
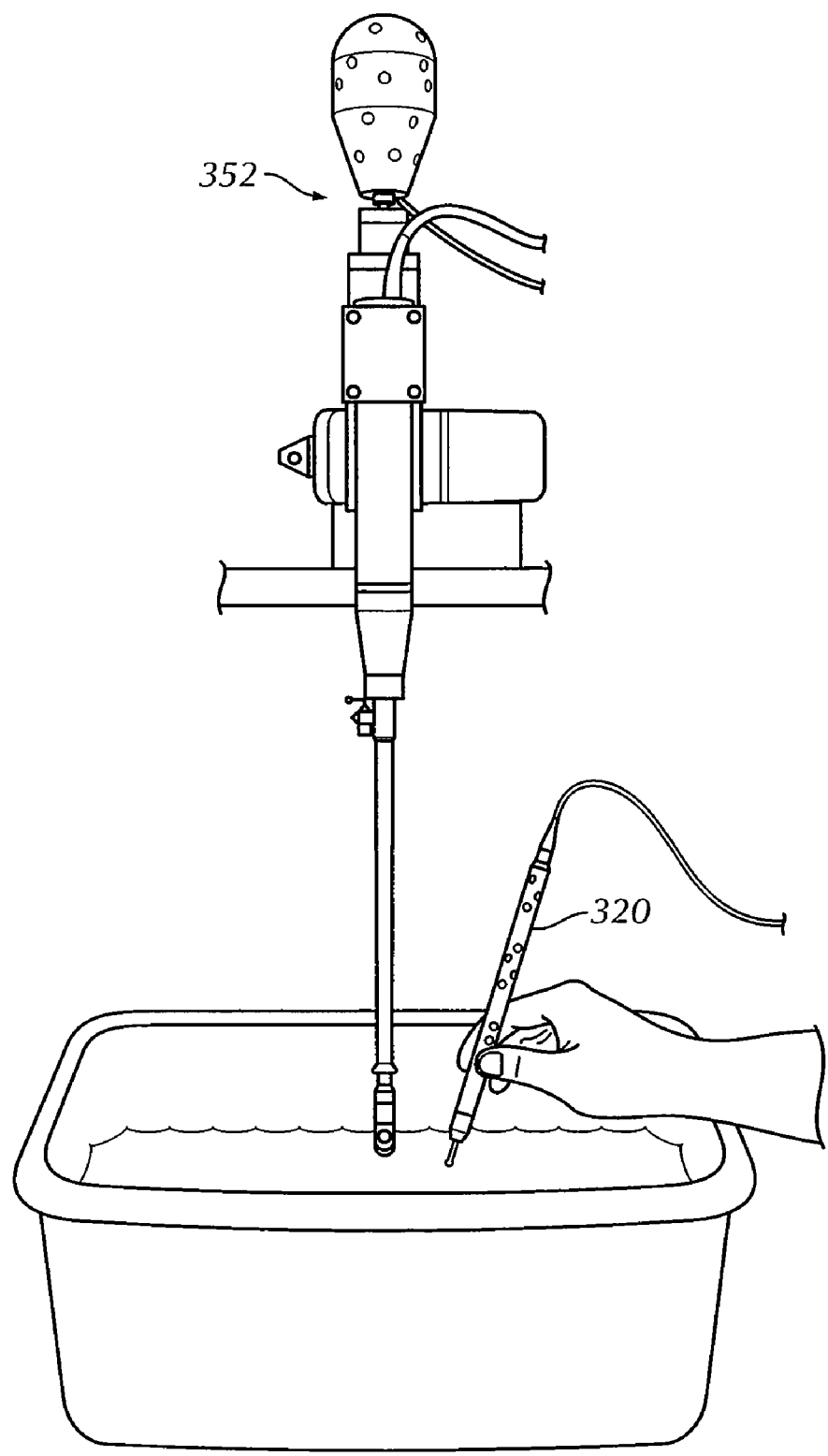
FIG. 3 is a perspective photographic view of the tracked endorectal ultrasonic (TERUS) probe of FIG. 2 being immersed in a water-bath for calibration.

For calibration, two rigid bodies are used that both have Infrared Light Emitting Diodes (IREDS) and are tracked by the optical tracking localization system. One rigid body 353 attached to the TERUS probe 352, and the TERUS probe 352 is securely fixed. The rotating tip of the TERUS probe 352 is immersed in a bath of water (FIG. 3) or other suitable material. The ERUS mounted rigid body 352 functions as a reference to which the second rigid body is tracked. The second rigid body is the pen probe 320 with a ball-tip such as a 3 mm ball-tip. The tip of the calibration probe 320 is placed into the beam of the TERUS probe 352 and can be seen as a bright spot in a corresponding ultrasound image (see FIG. 11 with the location of the ball tip circled). Using the ORION-based IGP system 300, which includes frame-grabbing capabilities, images along with the corresponding locations of the rigid bodies are acquired and saved. These images are processed to determine the "best-fit" plane through the points. The 2D location of the tip of the calibration pen probe 320 is determined in each of the images. A plurality of the 2D point locations are used to perform the calibration. The 2D locations are mapped to respective 3D locations using the Levenberg-Marquardt algorithm to solve for the resulting transformation matrix and the pixel to millimeter scale factors in the x and y directions. A subset of the acquired points or other acquired points can be used as an internal check of the precision of the plane. The software program selects the points in a random order, so each time the program is run, there is a potential for a different solution because of different points used. The software program then reports the average and maximum errors as well as the standard deviations for the calibration points and the check points. The program also reports the scale factors that are used to map pixels to millimeters and the transformation matrix of the calibrated beam to the rigid body attached to the ERUS transducer. One important error to observe is the RMS error of the check points (TRE). This is a quantification of plane fit quality. However, it is important to note that with one set of calibration data points, it is possible to get a variation in the checkpoint TRE. This is because the data points used to calculate the plane and the data points used to check the accuracy of the plane change each time the calibration is run.

It is generally desirable to recalibrate the TERUS probe 352 when the rigid body 353 is removed and then reattached to the TERUS probe 352, and/or when the ultrasound is transmitted at a different frequency or viewed at a different field of view from the previous calibration. The second condition is of interest to particular TERUS probe 352 described above because this TERUS probe 352 includes a multi-frequency transducer that is easily interchangeable among the three frequencies and different fields of view.

Figure 14:
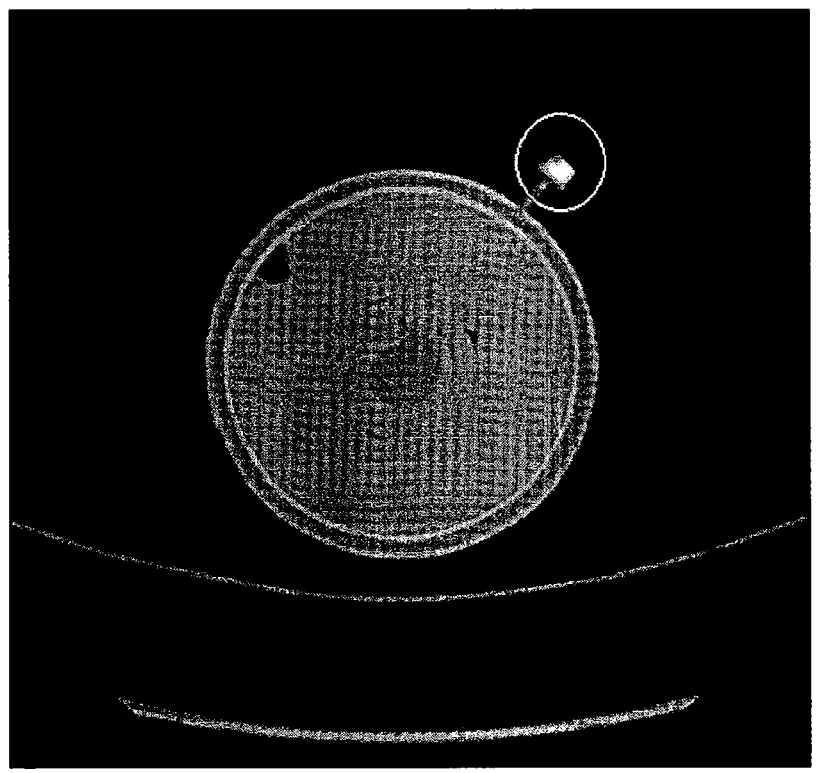
FIG. 14 a computed tomography (CT) image of a rectal phantom having a fiducial marker affixed thereto.

The next step is the registration of the CT volume to the physical space. This is accomplished by using the extrinsic fiducials 48 that are attached to the outside of the patient's body and using rigid registration techniques. The (x,y,z) locations of the fiducials 48 are found in the CT set and in physical space, and then registered using the quaternion method. To find the locations in CT space, a three-dimensional volume is created from the tomogram set. The fiducial caps 48 used in the scan are radio-opaque and show up bright in the images (see e.g., FIG. 14).

The centroid of each fiducial cap 48 is found using an intensity based approach and interpolation within slices to provide an accuracy of about half of the slice thickness. This process is known as super-resolution. As previously described, the physical space locations are then determined using the tracked physical space calibration probe 320. The rigid registration is then performed with a subset of the fiducials 48 from the two data sets. This registration creates a transformation matrix that rotates and translates one set of data to match the orientation of the other set. This transformation matrix, along with the average error of all of the fiducials 48, are calculated. An accurate fiducial registration error is necessary for, but does not guarantee, an accurate target registration error. Therefore, one fiducial 48 or an additional fiducial 48 can be used as a target, like in the calibration process, to check the accuracy of the FRE. The RMS error of the additional fiducial 48 is reported as the registration TRE.

The final stage in the process involves finding the (x,y,z) locations of the targets in the CT tomograms the same way that the fiducial locations were found. Then by using the output transformation matrix from the registration process, the locations of those points in physical space are calculated. The locations of the targets are also found using the TERUS probe 352, and their respective (x,y,z) locations in physical space are calculated using the transformation matrices from the calibration process and tracked image guided system. This provides two data sets containing the locations of the same targets in physical space located by two different methods. The values found using CT are taken to be the actual locations, and the values found using the TERUS probe 352 are compared to the actual. The distance between the locations of each target is then found, and is recorded as the target registration error (TRE). It should be noted that an accurate TRE is the only true verification of an accurately tracked system.

By optically tracking the TERUS probe 352 as data is collected, the intensity value for each pixel can be saved and then inserted into the nearest voxel in a corresponding volume matrix. Then validation of the accuracy of a volume reconstruction can be performed by finding the 3D coordinates of targets that are inside of the volume and comparing them to known physical locations. Over-determining the data placed into the volume around the area of interest is desirable so that speckle can be reduced and the signal to noise in the area will be improved by averaging a particular pixel's value from different images. Transformation of a 2D coordinate location in ultrasound image space into its corresponding 3D physical space occurs pixel by pixel and any unfilled voxels are left empty. It is contemplated that vector mathematics can be utilized to speed up the process. During the transformation process, the intensity value of each pixel is placed into the appropriate 3D voxel. Multiple intensity values that map to the same voxel in 3D space are handled. Preferably, arithmetic averaging is used when multiple intensity values are mapped to the same voxel such that the average of the multiple intensity values is placed into the voxel. Alternately, when multiple intensity values are mapped to the same voxel in 3D space, the intensity value is overwritten into the voxel.

By moving the ERUS probe in and around a particular portion of the anatomy to be imaged and tracking the probe's motion, one obtains a set of data points that represents the ultrasound image at particular point in the anatomy. Software is used to resolve the multiple data points into a single volumetric data point (voxel) for each point in the anatomy of interest. That allows one to construct a 3D image of that anatomy. The end result is a dataset consisting of ERUS voxels and their coordinates in the 3D image. Thus, one has obtained a "spatially-oriented" ultrasound image of the particular anatomy of interest. This is analogous to having the coordinates for any point in the volume, not just on the surface.

One can then manipulate (rotate, slice, pan, zoom, etc.) the data in any fashion desired to reconstruct views of the anatomy of interest from any perspective desired. This is analogous to the ability to manipulate CT and MRI images except the resolution of the internal detail is less than with either of these modalities; however, in colorectal ERUS is the current standard of care for tumor diagnosis.

The incorporation of IGP techniques to pre-operative staging, inter-operative visualization and post-operative follow-up of rectal cancer using TERUS improves the accuracy of staging, reduces the overall morbidity and mortality rates, and assists clinicians to detect and follow recurrences of rectal cancer over time. Accordingly, compiling the TERUS-obtained data into a library 100 (FIG. 11) of transrectal scans for interpretation. The library 100 may include scans of healthy patients, patients having tumors and, for patients having tumors, various stages of tumor growth.

Embodiments of the present invention create the 3D volumetric ultrasound images to create a library 100 (FIG. 11) of images (FIG. 14) that can be used for training via simulation. The library 100 and a means to display the data 310, such as a computer monitor 310 or a projector (not shown), can be used to provide interactive training of resident physicians, ultrasound technicians and nurses in effectively utilizing ultrasound technology.

Figure 11:
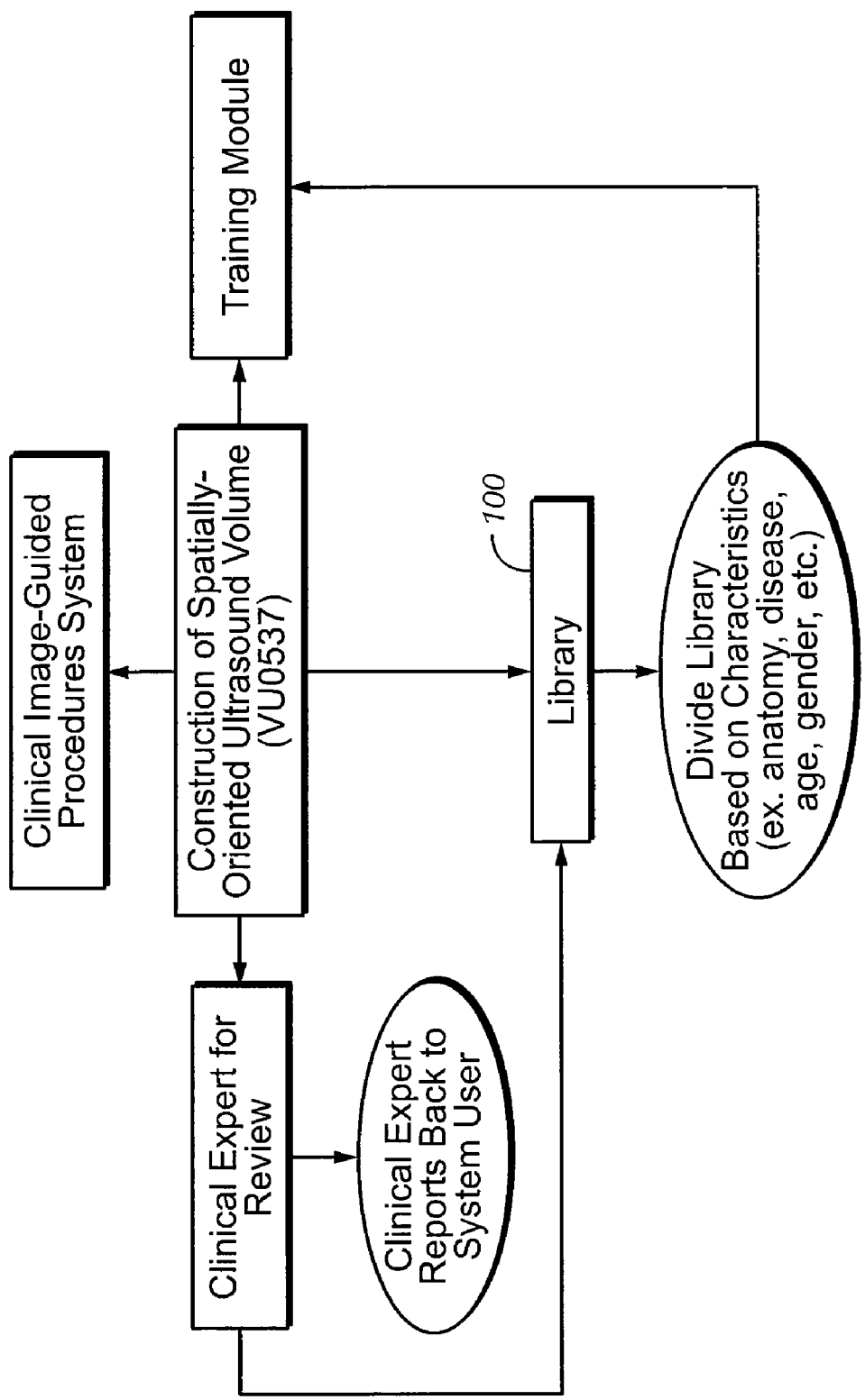
FIG. 11 shows a general flow chart for developing a training and diagnostics library in accordance with preferred embodiments of the present invention.
Figure 12:
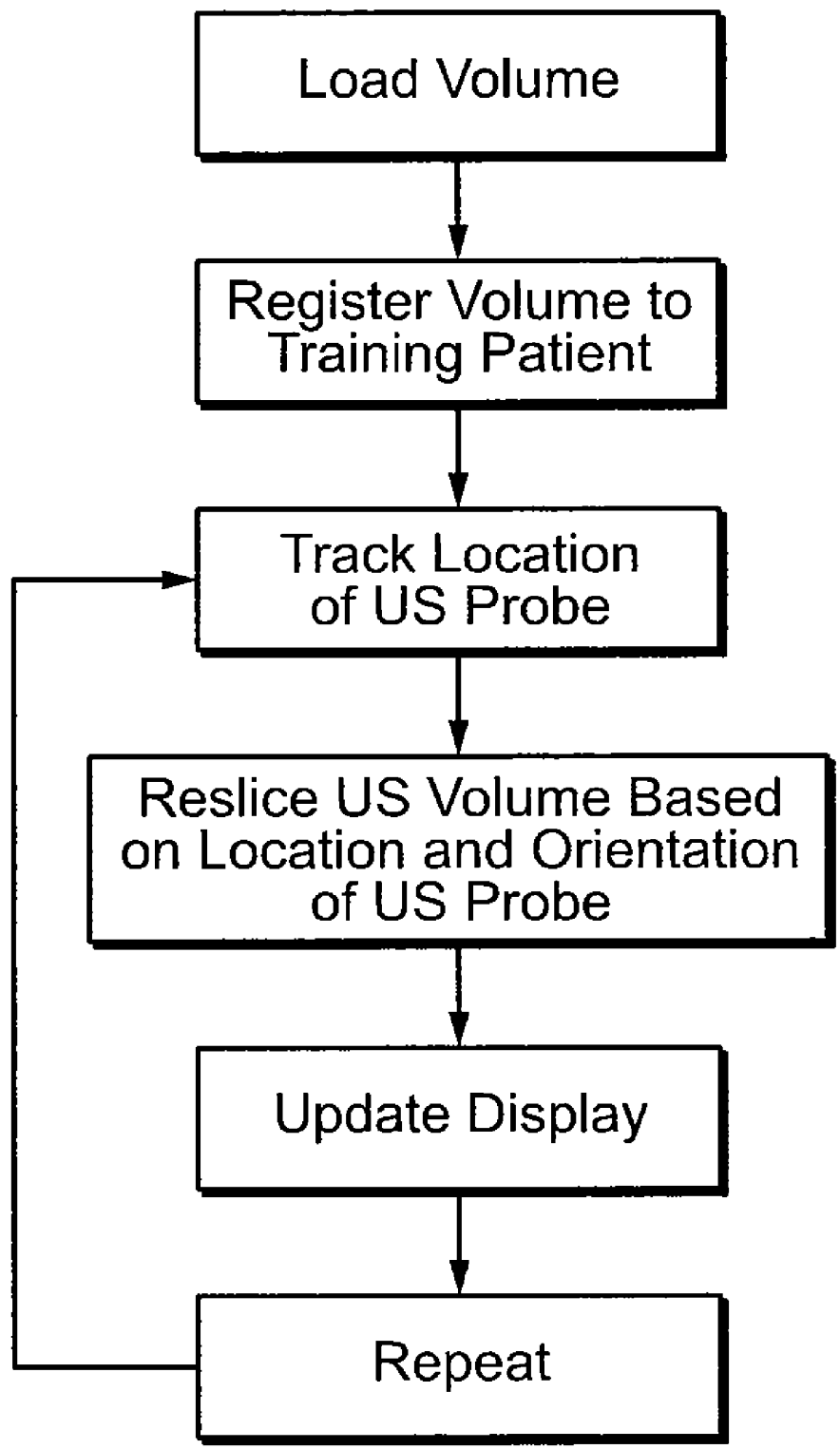
FIG. 12 shows a general flow chart for training using the training and diagnostics library of FIG. 11.

Referring to FIG. 11, the library 100 is created from 3D ultrasound volumes taken of multiple patients or multiple anatomies. The ultrasound-based IGP system 300 can acquire the images to be used in the library 100 and can be used for the training phase as well (FIG. 12). Preferably, the library 100 is developed by using the system 300 clinically. The more the ultrasound-based IGP system 300 is used, the larger the library 100 will become. The library 100 can be grouped based on patient characteristics, e.g., anatomy, disease, age, gender or the like. The specific volume sets can then be included back into the system 300.

It is contemplated that the library 100 is developed on a central server (not shown) by uploading data from a plurality of ultrasound-based IGP systems 300. The plurality of ultrasound-based IGP systems 300 can be networked or simply dial-up. The plurality of ultrasound-based IGP systems 300 may communicate through the internet. Alternatively, the library 100 may be developed by separate submissions to a common source for compilation onto a distributable storage medium such as a DVD, CD-ROM, Optical Disk or the like.

Although the ERUS technique was described above, the concept is readily adapted for training purposes for imaging other parts of the anatomy by using different ultrasound probes 352. Cardiac, OB/GYN, abdominal and carotid imaging all make wide use of ultrasound imaging.

The ultrasound-based IGP system 300 stores a library 100 of "spatially-oriented" images for various portions of the anatomy. A student practices the use of ultrasonography on a person such as his instructor or a classmate, but the images that are displayed would be those in the library 100. For example, suppose the instructor wanted to demonstrate and have the student practice the features of acquiring and understanding colorectal tumors. Referring to FIG. 12, the student actually manipulates the tracked ultrasound probe 352 or simulates motion of the tracked ultrasound probe 352 in use. The computer display 310 presents images of a tumor or an area of interest stored in the library 100 from many different geometric perspectives to facilitate understanding by the student. In this fashion it is envisioned that the training interval on real patients could be shortened by reducing (but not eliminating) the number of live patients on which the student must be trained.

The library 100 of spatially-oriented images stores a plurality of different patient datasets for training and comparison. One of the advantages of this system is that it can acquire the images to be used in the library and can be used for the training phase as well. FIG. 11 shows a general flow chart for developing the training and diagnostics library in accordance with preferred embodiments of the present invention. FIG. 12 shows a general flow chart for training using the training and diagnostics library.

Currently, modules exist to acquire data and produce spatially-oriented 3D images of the colorectal anatomy. The software for such is very modular and modules for cardiac, carotid, etc. can be readily added.

Of course, the preferred embodiments of the present invention are not limited to endorectal imaging and evaluation and may be utilized to analyze other anatomical regions of interest such as the vagina, the uterus, colon, upper intestine, throat and the like. The preferred embodiments may be utilized in conjunction with laparoscopic and endoscopic surgical techniques, as well, such as by inserting an ultrasonic probe 352 into a body through a cannula.

While described above as being used in combination with a CT scan, other imaging techniques such as PET, MRI or the like, may be utilized alone or in combination.

The ultrasound-based IGP system 300, when used with a second imaging technique (e.g., CT, PET, MRI or the like), enables other analyses such as size changes of a target (e.g., a tumor) in an anatomical region of interest (e.g., the rectum). Therefore, training using the combined imaging modalities stored in the library is also desirable.

The ultrasound-based IGP system 300 can also be used as a clinical tool for diagnosis of a disease. In this case a volume around a region of interest would be created and then sent to a clinical expert for evaluation. The clinical expert then reports the diagnosis. This information is sent back to the person who collected the data set and is also stored along with the image volume in the library.

The ultrasound-based IGP system 300 can be used as a clinical tool for the treatment of a disease. An ultrasound volume is created and loaded into the same or another ultrasound-based IGP system 300 for use during a procedure in the clinic or operating room (OR).

The present invention may be implemented with any combination of hardware and software. If implemented as a computer-implemented apparatus, the present invention is implemented using means for performing all of the steps and functions described above.

The present invention can be included in an article of manufacture (e.g., one or more computer program products) having, for instance, computer useable media. The media has embodied therein, for instance, computer readable program code means for providing and facilitating the mechanisms of the present invention. The article of manufacture can be included as part of a computer system or sold separately.

From the foregoing, it can be seen that the present invention comprises a method and apparatus for standardizing ultrasonography training using image to physical space registration of tomographic volumes from tracked ultrasound. It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

We claim:

1. A method for ultrasonography training using image to physical space registration of tomographic volumes from tracked ultrasound, the method comprising:
   (a) acquiring and storing a plurality of tomographic volumes from tracked ultrasound;
   (b) providing, for each of the stored tomographic volumes, a respective computer tomography (CT) volume that includes a first location of at least one target, the respective stored tomographic volumes each including a second location of the at least one target;
   (c) determining, for each of the stored tomographic volumes, a target registration error by calculating a distance between the first and second locations of the at least one target;
   (d) retrieving, using an image-guided procedure (IGP) system, one of the stored tomographic volumes;
   (e) using a tracked ultrasound probe coupled to the IGP system on a test patient; and
   (f) displaying images based on the retrieved volume that correlate to the physical space as determined by the position of the tracked ultrasound probe.

2. A method for ultrasonography diagnostics using image to physical space registration of tomographic volumes from tracked ultrasound, the method comprising:
   (a) providing a computer tomography (CT) volume that includes a first location of at least one target;
   (b) acquiring and storing a tomographic volume using an image-guided procedure (IGP) system having a tracked ultrasound probe, the tomographic volume including a second location of the at least one target;
   (c) determining a target registration error by calculating a distance between the first and second locations of the at least one target;
   (d) retrieving, using the IGP system, the stored tomographic volume;
   (e) using a tracked ultrasound probe coupled to the IGP system to perform off-line diagnosis of the patient by manipulating the stored tomographic volume; and
   (f) displaying images based on the retrieved volume that correlate to the physical space as determined by the position of the tracked ultrasound probe.

3. A method for performing an image guided procedure (IGP) using image to physical space registration of tomographic volumes from tracked ultrasound, the method comprising:
   (a) providing a computer tomography (CT) volume that includes a first location of at least one target;
   (b) acquiring a tomographic volume using an IGP system having a tracked ultrasound probe, the tomographic volume including a second location of the at least one target;
   (c) determining a target registration error by calculating a distance between the first and second locations of the at least one target;
   (d) retrieving, using the IGP system, the stored tomographic volume;
   (e) using a tracked instrument coupled to the IGP system to perform the IGP; and
   (f) displaying images based on the retrieved tomographic volume that correlate to the physical space as determined by the position of the tracked instrument.

* * * * *